Figure 1:
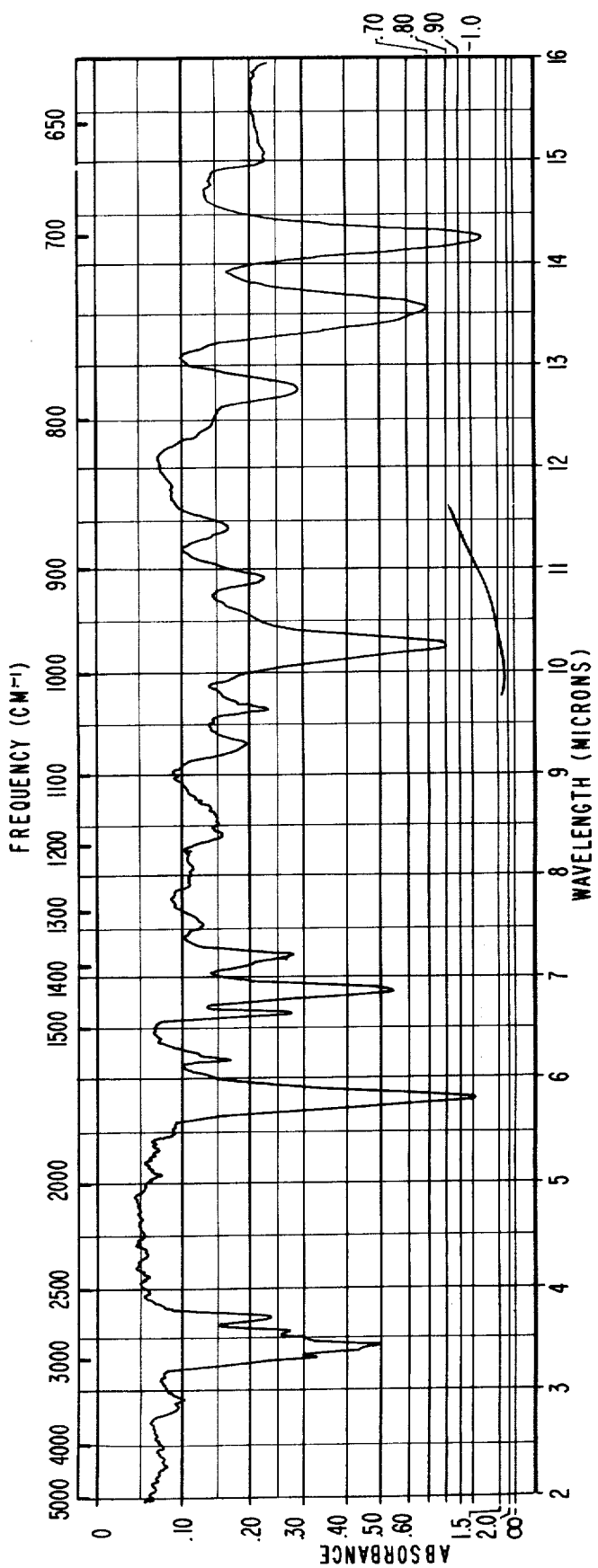

United States Patent [19]

Hall et al.

[11] 4,010,207
[45] Mar. 1, 1977

[54] PROCESS FOR THE ALKYLATION OF α,β-UNSATURATED ALDEHYDES

[75] Inventors: John B. Hall, Rumson; Wilhelmus Johannen Wiegers, Red Bank, both of N.J.

[73] Assignee: International Flavors & Fragrances Inc., New York, N.Y.

[22] Filed: Jan. 15, 1976

[21] Appl. No.: 649,552

[52] U.S. Cl. .......................................... 260/601 R
[51] Int. Cl.² .......................................... C07C 47/20
[58] Field of Search ............................... 260/601 R

[56] References Cited

FOREIGN PATENTS OR APPLICATIONS 1,811,517  7/1969  Germany .................. 260/601 R

OTHER PUBLICATIONS

Graaf et al., "Tetrahedron Letters," No. 17 (1974), pp. 1653–1656.
Tsukusa et al., "Chemical Abstracts" vol. 81, (1974), p. 135,501g.
Dietl et al., "Tetrahedron Lett." (1973), p. 1273.
Kovats, "Chemical Abstract" vol. 74 (1971), p. 459.

*Primary Examiner*—James O. Thomas, Jr.
*Assistant Examiner*—W. B. Lone
*Attorney, Agent, or Firm*—Arthur L. Liberman; Franklin D. Wolffe

[57] ABSTRACT

A process is described for the preparation of alpha substituted unsaturated aldehydes according to the reaction:

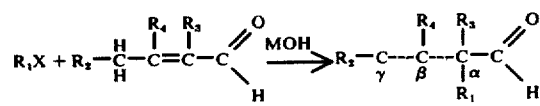

wherein one of the dashed lines is a double bond and the other of the dashed lines is a single bond; wherein $R_1$ is allyl or benzyl, $R_2$ is one of alkyl, aryl, alkenyl or alkoxyalkyl and $R_3$ and $R_4$ are each hydrogen or alkyl, with the proviso that when $R_3$ is alkyl the dashed line between the $\beta$ carbon atom and the $\gamma$ carbon atom represents a double bond and when $R_3$ is hydrogen, either of the dashed lines is a double bond, wherein X is chloro or bromo, and wherein M is alkali metal, the reaction being carried out (1) using a phase transfer agent, and (2) in a two phase system.

Also described is the novel compound, 2,4,7-trimethyl-2,6-octadienal having uses in altering, modifying or enhancing the organoleptic properties of foodstuffs, perfume compositions and perfumed articles.

7 Claims, 3 Drawing Figures

IR SPECTRUM

EXAMPLE II
IR SPECTRUM

EXAMPLE VIII

IR SPECTRUM FOR FRACTION 26 Major Peak

PROCESS FOR THE ALKYLATION OF α, β-UNSATURATED ALDEHYDES

SCHEME A

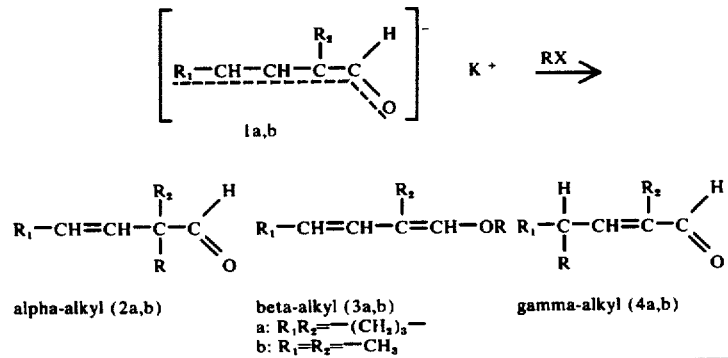

alpha-alkyl (2a,b)  beta-alkyl (3a,b)  gamma-alkyl (4a,b)
a: $R_1,R_2=-(CH_2)_3-$
b: $R_1=R_2=-CH_3$

BACKGROUND OF THE INVENTION

Alpha substituted unsaturated aldehydes having the structure:

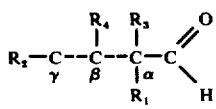

wherein one of the dashed lines is a double bond and the other of the dashed lines is a single bond; wherein $R_1$ is allyl or benzyl, $R_2$ is one of alkyl, aryl, alkenyl or alkoxyalkyl and $R_3$ and $R_4$ are each hydrogen or alkyl, with the proviso that when $R_3$ is alkyl the dashed line between the β carbon atom and the γ carbon atom represents a double bond and when $R_3$ is hydrogen, either of the dashed lines is a double bond, are valuable substances useful in the formulation of perfumery, tobacco and food flavoring materials, in the preparation of polymers and as intermediates for the preparation of pharmaceutical substances.

German Pat. No. 1,244,784, issued on July 20, 1967, discloses the reaction:

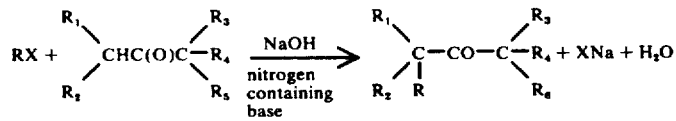

wherein R can be one of alkyl, alkenyl, allyl, propargyl, cyclohexyl or benzyl; X is chloro or bromo and $R_1$, $R_2$, $R_3$, $R_4$ and $R_5$ can be hydrogen, alkyl, alkenyl or phenyl. The reaction of the German Patent is limited to ketones. Although such ketones could be unsaturated, the nature of the reaction is different in kind from the reaction of the instant invention.

De Graff, et al, Tetrahedron Letters, 17, pages 1653–56, 1974, teaches that both 1-cyclohexene carboxaldehyde and 2-methyl-2-pentene-1-al could be converted into their respective anions by reaction with a small excess of potassium amide in liquid ammonia at −60° C and that treatment of these anions with reactive alkylating agents gives moderate to good yields, according to the following reaction scheme:

Whereas the reaction of the instant invention is commercially feasible, the De Graff, et al. reaction, taking place with potassium amide in liquid ammonia at a very low temperature, gives rise to a reaction system having little commercial feasibility and gives rise to a mixture of products.

Chemical Abstracts, 135501 g, 1974, summarizes a paper by Tsukasa, et al. entitled: "Alkylation of alpha, beta-unsaturated cyclic ketones. Synthesis of jasmones". In this case cis and trans jasmones are synthesized by reaction of 3-methyl-2-cyclopentenone with an alkyl halide in the presence of powdered potassium hydroxide and dimethyl sulfoxide; the Chemical Abstracts synthesis being carried out with dimethyl sulfoxide on a ketone rather than an aldehyde. This process is different in kind from the process of the instant invention.

THE INVENTION

The invention accordingly comprises the novel process and steps, specific embodiments of which are also described hereinafter by use of experiments and in accordance with what is now the preferred practice of the invention.

The process of the invention comprises reacting alpha, beta unsaturated aldehyde compounds with allylic halides or with benzylic halides in the presence of an inert solvent alkali metal hydroxides and in the presence of a "phase transfer agent". The reaction is carried out in a two phase system. Thus, our invention is generically illustrated by the following reaction:

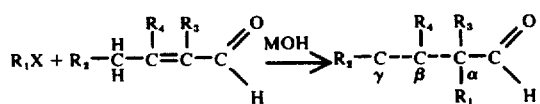

wherein one of the dashed lines is a double bond and the other of the dashed lines is a single bond; wherein $R_1$ is allyl or benzyl, $R_2$ is one of alkyl, aryl, alkenyl or alkoxyalkyl and $R_3$ and $R_4$ are each hydrogen or alkyl, with the proviso that when $R_3$ is alkyl the dashed line between the $\beta$ carbon atom and the $\gamma$ carbon atom represents a double bond and when $R_3$ is hydrogen, either of the dashed lines is a double bond, wherein X is chloro or bromo and wherein M is alkali metal.

More specifically, our invention provides a process for the alkylation of alpha, beta unsaturated aldehydes with reactive allylic halides or benzylic halides under the influence of a base, comprising the step of placing the reactants for the process and the base, respectively in two immiscible phases; an organic phase and either (i) an aqueous base phase or (ii) a solid base phase with the reactants being located substantially entirely in the first mentioned organic phase and the base being located substantially entirely in the second mentioned phase; and adding to this two phase system a "phase transfer agent" which may be one or more of several organic quaternary ammonium salts.

Specific examples of phase transfer agents useful in our invention are as follows:

Tricapryl methyl ammonium chloride;
Cetyl trimethyl ammonium bromide; and
Benzyl trimethyl ammonium hydroxide.

In general, the phase transfer agents most preferred have the generic formula:

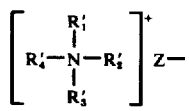

wherein at least one of $R_1'$, $R_2'$, $R_3'$ and $R_4'$ is $C_6-C_{14}$ aryl, $C_6-C_{10}$ alkyl, $C_6-C_{14}$ alkaryl and $C_6-C_{20}$ alkenyl and the other of $R_1'$, $R_2'$, $R_3'$ and $R_4'$ is alkyl such as methyl, ethyl, n-propyl, i-propyl, 1-butyl, 2-butyl, 1-methyl-2-propyl, 1-pentyl and 1-octyl and $Z^-$ is an anion such as chloride, bromide and hydroxide.

The process of our invention is carried out in an inexpensive solvent which is inert to the reaction system such as toluene, benzene, o-xylene, m-xylene, p-xylene, ethyl benzene, n-hexane, cyclohexane, methylene chloride and o-dichlorobenzene.

The process of our invention is carried out at a temperature in the range of from about 10° C up to about 150° C with a temperature range of 50°-120° C being preferred. The reaction time is inversely proportional to the reaction temperature, with lower reaction temperatures giving rise to greater reaction times; and, accordingly, the reaction time ranges from about 30 minutes up to about 10 hours.

In the reaction of our invention the mole ratio of alpha, beta unsaturated reactants to allyl or benzyl halide reactants is in the range of from 0.5:1.5 up to about 1.5:0.5 with a preferred ratio of alpha, beta unsaturated aldehydes to allylic or benzylic halides being from about 1:1 up to about 1:1.2.

The mole ratio of base to allylic or benzylic halides in the reaction mass may be in the range of from about 0.75:1 up to about 1.5:1 with a preferred ratio of base-:allylic or benzylic halides being from about 1:1 up to about 1.2:1.

The quantity of "phase transfer agent" in the reaction mass based on the amount of alpha, beta unsaturated aldehydes in the reaction mass may vary from 0.5 gram per mole of aldehyde up to 25 grams of "phase transfer agent" per mole of aldehyde with a preferred concentration of "phase transfer agent" being in the range of from about 2.5 up to about 7.5 grams of "phase transfer agent" per mole of alpha, beta unsaturated aldehyde.

The reaction of our invention is preferably carried out at atmospheric pressure since that is the most convenient condition. However, lower or higher pressures can be used without detrimentally affecting the ultimate yield of desired reaction product.

Specific examples of the reactions intended to be encompassed by the process of our invention and the product(s) produced thereby are set forth below. It is noteworthy that the reaction products can be used "as is" for their organoleptic properties, or they may be separated using conventional separation techniques, e.g. fractional distillation.

2,5-Dimethyl-2-Propenyl Hex-4-enal

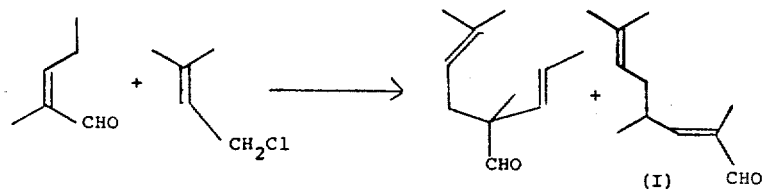

2-Methyl-2-Benzyl-Pent-3-enal

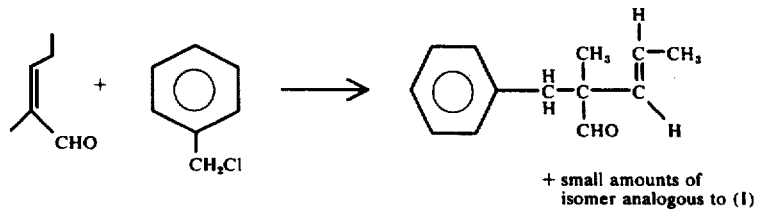

+ small amounts of isomer analogous to (I)

2-Butenyl-2-Ethyl-5-Methyl-Hex-4-enal

-continued

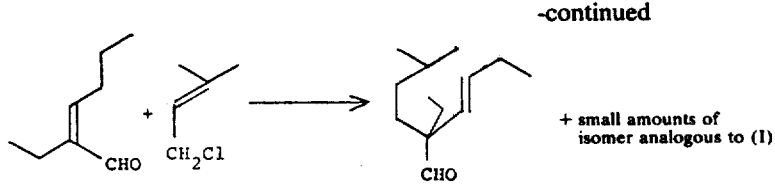

2-Benzyl-2-Ethyl-Hex-3-enal

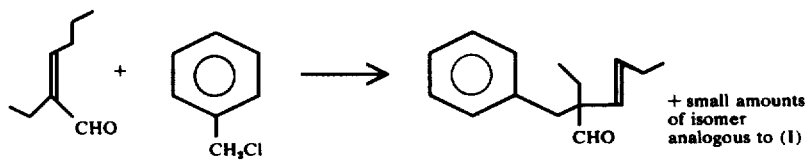

2-Prenyl Citral

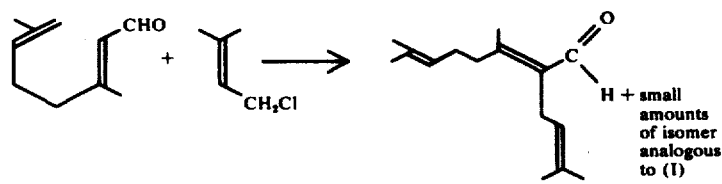

2-Prenyl Nonenal

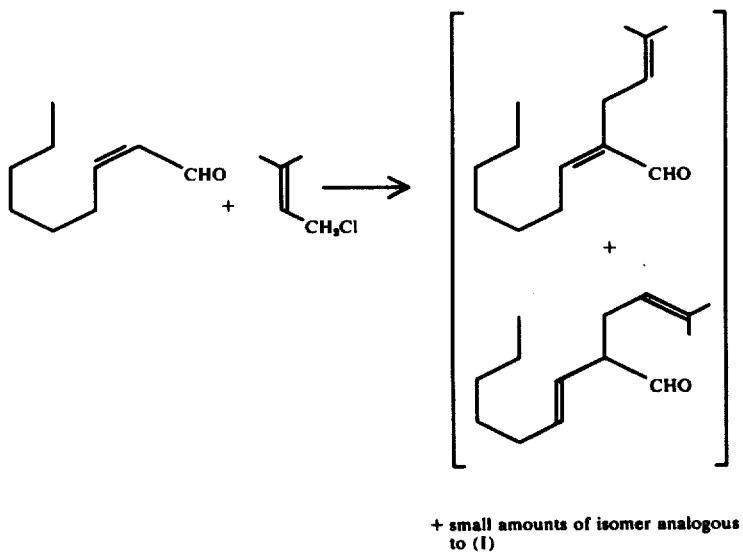

The particular base used in the reaction is not critical but, preferred are, sodium hydroxide and potassium hydroxide.

The compounds produced according to the process of our invention are useful interalia, for producing perfume compositions. Thus, for example, 2,5-dimethyl-2-propenyl hex-4-enal has a tart, green, citrus, cumin, sweet, carvone-like note and a lavandulol-like nuance. 2-Benzyl-2-ethyl-hex-3-enal has a sweet, floral, rosey note. 2-Butenyl-2-ethyl-5-methyl-hex-4-enal has a green, sweet, tomato-like aroma with a citrus character and a rosey, floral note. 2-Methyl-2-benzyl-pent-3-enal has a sweet, fruity, citrusy, floral, green aroma. 2-Prenyl citral has a sweet, green orangy aroma with woody, citrus and resinous notes. In tobacco, in the mainstream on smoking, 2-prenyl citral has a spicy, coriander-like aroma and in the sidestream it has a woody effect. As a foodstuff flavor 2-prenyl citral has a sweet, coriander, citral and spicy flavor character.

The compound 2,4,7-trimethyl-2,6-octadienal is a novel compound. Insofar as its flavor properties are concerned, this compound has a lemon, citral-like, mandarin aroma with a tangerine nuance, and a lemon, citral mandarin taste with a tangerine nuance at 0.2 ppm. Its threshold level is 0.05 ppm. It is useful in altering, enhancing or modifying the citrus (especially lemon) flavor or aroma of citrus or lemon flavored foodstuffs.

The terms "alter" and "modify" in their various forms will be understood herein to mean the supplying or imparting of a flavor character or note to an otherwise bland, relatively tasteless substance, or augmenting an existing flavor characteristic where the natural flavor is deficient in some regard, or supplementing the existing flavor or aroma impression to modify the organoleptic character. The materials which are so altered are generally referred to herein as consumable materials.

The term "enhance" in its various forms will be understood herein to mean the intensification of a given flavor and/or aroma "nuance" or "note" in a food flavor composition and/or in a foodstuff without changing the type or quality of said flavor or aroma nuance or note.

The term "foodstuff" as used herein includes both solid and liquid ingestible materials for man or animals, which materials usually do, but need not, have nutritional value. Thus, foodstuffs includes fruit juices, meats, gravies, soups and convenience foods, vegetables, snack foods, dog and cat foods, other veterinary products, and the like.

When the 2,4,7-trimethyl-2,6-octadienal according to this invention is used in a food flavoring composition, it can be combined with conventional flavoring materials or adjuvants. Such co-ingredients or flavor adjuvants are well known in the art for such use and have been extensively described in the literature. Apart from the requirement that any such adjuvant material be ingestibly acceptable, and thus non-toxic or otherwise non-deleterious, conventional materials can be used and broadly include other flavor materials, vehicles, stabilizers, thickeners, surface active agents, conditioners, and flavor intensifiers.

Examples of preferred co-flavoring adjuvants are:
Natural Orange Oil;
Acetaldehyde;
Ethyl Acetate;
Ethyl Butyrate;
Propanal;
Trans-2-hexenal;
Trans-2-ethylidene-cis-3-hexenal;
2-ethylidene-6-methyl-cis-3-heptenal; and
Cis-2-ethylidene-cis-3-hexenal The 2,4,7-trimethyl-2,6-octadienal or the compositions incorporating it, as mentioned above, can be combined with one or more vehicles or carriers for adding it to the particular product. Vehicles can be edible or otherwise suitable materials such as ethyl alcohol, propylene glycol, water and the like. Carriers include materials such as gum arabic, carragennan, other gums, and the like. The 2,4,7-trimethyl-2,6-octadienal according to this invention can be incorporated with the carriers by conventional means such as spray-drying, drum-drying, and the like. Such carriers can also include materials for coacervating the 2,4,7-trimethyl-2,6-octadienal (and other flavoring ingredients, as present) to provide encapsulated products. When the carrier is an emulsion the flavoring composition can also contain emulsifiers such as mono- and diglycerides of fatty acids and the like. With these carriers or vehicles, the desired physical form of the composition can be prepared.

The quantity of 2,4,7-trimethyl-2,6-octadienal utilized should be sufficient to impart the desired flavor characteristic to the product, but on the other hand, the use of an excessive amount of the derivative is not only wasteful and uneconomical, but in some instances too large a quantity may unbalance the flavor or other organoleptic properties of the product consumed. The quantity used will vary depending upon the ultimate foodstuff; the amount and type of flavor initially present in the foodstuff; the further process or treatment steps to which the foodstuff will be subjected; regional and other preference factors; the type of storage, if any, to which the product will be subjected; and the preconsumption treatment, such as baking, frying, and so on, given to the product by the ultimate consumer. Accordingly, the terminology "effective amount" and "sufficient amount" is understood in the context of the present invention to be quantitatively adequate to alter, modify or enhance the flavor of the foodstuff.

It is accordingly preferred that the ultimate compositions contain from about 0.08 parts per million (ppm) to about 250 ppm of 2,4,7-trimethyl-2,6-octadienal. More particularly, in food compositions, it is desirable to use from about 0.15 ppm to 50 ppm for enhancing or modifying flavors and in certain preferred embodiments of the invention, from about 0.2 to 10 ppm of the 2,4,7-trimethyl-2,6-octadienal included to add positive citrusy flavors to the finished product. All parts, proportions, percentages and ratios herein are by weight unless otherwise indicated.

The amount of 2,4,7-trimethyl-2,6-octadienal of our invention to be utilized in flavoring compositions can be varied over a wide range depending upon the particular quality to be added to the foodstuff. Thus, amounts of 2,4,7-trimethyl-2,6-octadienal according to the present invention, of from about 1 up to 80 or 90 percent of the total flavoring composition can be incorporated in such compositions. It is generally found to be desirable to include from about 2 up to about 20 percent of the 2,4,7-trimethyl-2,6-octadienal in such compositions.

Insofar as its perfume properties are concerned, this compound has an excellent lemon citrus character useful for imparting lemon nuances to citrus type perfume compositions and essential oils.

The following Examples I–VI and VIII and IX serve to illustrate embodiments of our invention as it is now preferred to practice it. Example VII illustrates a utility of the compounds produced according to the process of our invention. It will be understood that these Examples are illustrative and restricted thereto only as defined in the appended claims.

EXAMPLE I

PREPARATION OF 2,5-DIMETHYL-2-PROPENYL HEX-4-ENAL

Into a 1 liter reaction flask equipped with stirrer, thermometer, reflux condenser and addition funnel are added a solution of 72 grams of sodium hydroxide in 72 grams of water. 80 Grams of toluene and 5 grams of tricapryl methyl ammonium chloride (ALIQUAT 336, produced by General Mills Chemicals, Inc.) are then added to the mixture. The mixture is heated to a temperature in the range of 75°–80° C with stirring. Over a period of 6 hours, a solution of 200 grams of 2-methyl-pent-2-enal and 210 grams of prenyl chloride is added to the reaction mass. At the end of the 6 hour period, the reaction mass is stirred at 75°–80° C for another 4 hours. At the end of the 4 hour period the organic layer is separated, washed neutral and the solvent stripped off.

The residual oil is then distilled on a 12 inch Vigreaux column after adding 10 grams Primol and 1 gram Ionox. The fractions taken off the column are as follows:

| Fraction No. | Vapor Temperature (° C) | Liquid Temperature (° C) | Vac. mm Hg | Weight (g) |
| --- | --- | --- | --- | --- |
| 1 | 64–75 | 93–110 | 44–44 | 24.4 |
| 2 | 115 | 123 | 44 | 23.9 |
| 3 | 118 | 131 | 44 | 52.3 |
| 4 | 119 | 139 | 44 | 52.8 |
| 5 | 121 | 168 | 44 | 39.7 |
| 6 | 138 | 190 | 44 | 17.2 |

Fractions 2–5 are bulked and re-distilled on a 12 plate Vigreaux column at a reflux ratio of 12:1 after adding thereto 8 grams of Primol and 0.4 grams of Ionox. The Fractional Distillation Data is as follows:

| Fraction No. | Vapor Temperature (° C) | Liquid Temperature (° C) | Vac. mm Hg | Weight (g) |
| --- | --- | --- | --- | --- |
| 1 | 55–58 | 106 | 44–44 | 1.1 |
| 2 | 68 | 108 | 44 | 3.3 |
| 3 | 94 | 109 | 32 | 4.2 |
| 4 | 108 | 111 | 38 | 3.0 |
| 5 | 112 | 112.5 | 38 | 5.2 |
| 6 | 112 | 113 | 38 | 6.6 |
| 7 | 115 | 115 | 38 | 7.3 |
| 8 | 114 | 115 | 38 | 8.3 |
| 9 | 114 | 116 | 38 | 8.6 |
| 10 | 115 | 118 | 38 | 11.3 |
| 11 | 115 | 118 | 38 | 8.5 |
| 12 | 115 | 118 | 38 | 9.1 |
| 13 | 115 | 120 | 38 | 8.0 |
| 14 | 115 | 120 | 38 | 8.1 |
| 15 | 116 | 120 | 38 | 11.0 |
| 16 | 117 | 120 | 38 | 10.4 |
| 17 | 117 | 120 | 38 | 9.2 |
| 18 | 118 | 120 | 38 | 4.7 |
| 19 | 112–114 | 122–123 | 38–38 | 4.7 |
| 20 | 114 | 131 | 38 | 10.5 |
| 21 | 120 | 151 | 38 | 9.0 |
| 22 | 123 | 230 | 38 | 5.5 |

Fractions 10–19 are analyzed using GLC, NMR and IR analyses which confirm that the major component is the compound, 2,5,-dimethyl-2-propenyl hex-4-enal. This material has a tart, green, citrus, cumin, sweet, carvone-like note with a lavandulol-like nuance.

EXAMPLE II

PREPARATION OF 2-METHYL-2-BENZYL-PENT-3-ENAL

Into a 1 liter reaction flask equipped with stirrer, thermometer, reflux condenser and addition funnel are placed a solution of 72 grams of sodium hydroxide in 72 grams of water. 80 Grams of toluene and 5 grams of tricapryl methyl ammonium chloride are then added to the NaOH solution. The resulting mixture is heated to a temperature in the range of 75°–80° C. While maintaining the temperature at 75°–80° C and over a 6 hour period, a solution of 200 g of 2-methyl pent- 2-enal and 253 grams of benzyl chloride is added to the reaction mass. The reaction mass is then stirred for another 6 hours while maintaining the temperature in the range of 75°–80° C. The reaction mass is then refluxed for a period of 2.5 hours in order to cause the remaining benzyl chloride to be reacted. The organic layer is separated, washed neutral and the solvent stripped off.

The residual oil is then distilled on a 3 inch Splash column after adding thereto 14 grams of Primol and 1 gram of Ionox. The distillation data is as follows:

| Fraction No. | Vapor Temperature (° C) | Liquid Temperature (° C) | Vac. mm Hg | Weight (g) |
| --- | --- | --- | --- | --- |
| 1 | 79–100 | 137–142 | 50–50 | 8.9 |
| 2 | 113 | 152 | 50 | 18.1 |
| 3 | 150 | 165 | 50 | 27.7 |
| 4 | 166 | 121 | 50 | 47.8 |
| 5 | 168 | 180 | 50 | 59.6 |
| 6 | 170 | 185 | 50 | 48.8 |
| 7 | 172 | 218 | 50 | 37.8 |
| 8 | 175 | 242 | 50 | 22.1 |
| 9 | 200 | 250 | 50 | 8.3 |

Fractions 4–8 are bulked and this material is distilled on a 10 inch column (reflux ratio 9:1) containing large stone packing, after adding thereto 6 grams of Primol and 0.5 grams of Ionox. The Fractional Distillation Data is as follows:

| Fraction No. | Vapor Temperature (° C) | Liquid Temperature (° C) | Vac. mmHg | Weight (g) |
| --- | --- | --- | --- | --- |
| 1 | 90–94 | 116–117 | 3.0–3.0 | 2.7 |
| 2 | 103 | 118 | 3.0 | 5.8 |
| 3 | 109 | 118 | 3.0 | 6.3 |
| 4 | 114 | 118 | 3.0 | 7.9 |
| 5 | 112 | 117 | 2.9 | 10.2 |
| 6 | 113 | 117 | 3.0 | 15.2 |
| 7 | 113 | 118 | 3.0 | 14.7 |
| 8 | 113 | 118 | 3.0 | 14.0 |
| 9 | 113 | 118 | 3.0 | 14.3 |
| 10 | 113 | 118 | 3.0 | 15.5 |
| 11 | 113 | 119 | 3.0 | 13.2 |
| 12 | 113 | 120 | 3.0 | 14.2 |
| 13 | 113 | 120 | 3.0 | 10.6 |
| 14 | 113 | 124 | 3.0 | 15.0 |
| 15 | 116 | 135 | 3.0 | 14.1 |
| 16 | 119 | 172 | 3.0 | 13.9 |
| 17 | 124 | 196 | 3.0 | 7.4 |
| 18 | 118 | 250 | 3.0 | 6.0 |

Fractions 6–8 are bulked and analyzed using GLC, NMR and IR analyses which confirm that the resulting material is 2-methyl-2-benzyl-pent-3-enal. This material has a sweet, fruity, citrusy, floral, green aroma. The IR spectrum for 2-methyl-2-benzyl-pent-3-enal (Fraction 5) is set forth in FIG. 1.

EXAMPLE III

PRODUCTION OF 2-PRENYL CITRAL
3,7-dimethyl-2(3-methyl-2-butenyl)2,6-octadienal)

Into a 1 liter reaction flask equipped with condenser, stirrer, thermometer, heating mantle and addition funnel are placed a solution of 61 grams of sodium hydroxide in 61 grams of water. 61 Grams of toluene and 13.6 grams of tricapryl methyl ammonium chloride are then added to the NaOH solution. The resulting mixture is heated to reflux (102° C) and while the toluene-sodium hydroxide mixture is refluxing, over a 1 hour period, a solution of 215 grams of citral and 153 grams of prenyl chloride is added. After the addition is complete, the reaction mass is refluxed for an additional 1 hour. At this point, 200 ml water is added, the reaction mass is stirred for 15 minutes and then transferred into a separatory funnel. The organic layer is separated, washed neutral and the solvent stripped off.

The residual oil is then distilled at 2.5 mm Hg through a 6 inch Vigreaux column, after adding thereto 10.9 grams of Primol and 1 gram of Ionox. The Fractional Distillation data is as follows:

| Fraction No. | Vapor Temperature (° C) | Liquid Temperature (° C) | Weight (g) |
| --- | --- | --- | --- |
| 1 | 51 | 106 | 8.0 |
| 2 | 64 | 134 | 11.1 |
| 3 | 102 | 133 | 10.1 |
| 4 | 118 | 138 | 13.1 |
| 5 | 122 | 141 | 15.1 |
| 6 | 125 | 148 | 32.8 |
| 7 | 127 | 154 | 23.7 |
| 8 | 127 | 159 | 24.0 |
| 9 | 135 | 176 | 19.9 |
| 10 | 142 | 184 | 15.4 |
| 11 | 164 | 195 | 24.2 |

Fractions 5–9 are bulked and distilled on an 8 plate Vigreaux column after adding thereto 3 grams of Primol and 0.5 grams of Ionox. The Fractional Distillation Data is as follows:

| Fraction No. | Vapor Temperature (° C) | Liquid Temperature (° C) | Vac. mm Hg | Weight (g) |
| --- | --- | --- | --- | --- |
| 1 | 107–139 | 150–156 | 3.1 | 4.8 |
| 2 | 141 | 155 | 3.0 | 4.8 |
| 3 | 143 | 155 | 3.0 | 5.8 |
| 4 | 144 | 156 | 3.0 | 8.1 |
| 5 | 144 | 157 | 2.6 | 7.5 |
| 6 | 144 | 160 | 2.6 | 11.1 |
| 7 | 140 | 162 | 2.5 | 7.0 |
| 8 | 144 | 176 | 2.4 | 8.7 |
| 9 | 146 | 214 | 2.4 | 7.3 |
| 10 | 138 | 250 | 2.4 | 6.1 |

Fractions 3–8 are bulked and analyzed using NMR, IR and GLC analyses which confirm that the resulting product is 2-prenyl citral. This material has a sweet, creamy, orangy note with woody, citrusy and resinous nuances.

EXAMPLE IV

Production of 2-butenyl-2ethyl-5-methyl hex-4-enal

Into a 1 liter reaction flask equipped with stirrer, thermometer, condenser, addition funnel, heating mantle and Thermo-watch are placed a solution of 72 grams of sodium hydroxide and 72 grams of water. 81 grams of toluene and 5 grams of tricapryl methyl ammonium chloride is then added and the mixture is heated with stirring to a temperature in the range of 75°–90° C. Over a period of 6 hours, a solution of 252 grams of 2-ethyl hex-2-enal and 215 grams prenyl chloride is added to the reaction mass while maintaining the temperature at 75°–80° C. After addition is complete the reaction mass is stirred for a period of 4 hours at 75°–80° C. The organic layer is separated, washed neutral and the solvent stripped off. 13 Grams of Primol is then added to the residual oil and the residual oil is distilled at 2.5 mm Hg on a rush-over column yielding the following fractions:

| Fraction No. | Vapor Temperature (° C) | Liquid Temperature (° C) | Weight (g) |
| --- | --- | --- | --- |
| 1 | 40 | 57 | 14.8 |
| 2 | 47 | 62 | 22.9 |
| 3 | 51 | 58 | 15.4 |
| 4 | 54 | 71 | 18.0 |
| 5 | 58 | 73 | 23.4 |
| 6 | 67 | 83 | 17.9 |
| 7 | 80 | 89 | 13.4 |
| 8 | 83 | 92 | 26.6 |
| 9 | 85 | 92 | 22.3 |
| 10 | 85 | 94 | 19.0 |
| 11 | 85 | 99 | 18.5 |
| 12 | 87 | 98 | 16.8 |
| 13 | 94 | 119 | 26.9 |
| 14 | 130 | 160 | 19.5 |
| 15 | 195 | 250 | 22.8 |

Fractions 5–14 are bulked and re-distilled at 2.5 mm Hg at a reflux ratio of 9:1 on a 12 plate Vigreaux column after adding thereto 5.1 grams of Primol and 0.5 gram Ionox. The following fractions are recovered:

| Fraction No. | Vapor Temperature (° C) | Liquid Temperature (° C) | Weight (g) |
| --- | --- | --- | --- |
| 1 | 44 | 88 | 8.1 |
| 2 | 50 | 95 | 6.9 |
| 3 | 93 | 117 | 13.7 |
| 4 | 96 | 119 | 9.2 |
| 5 | 97 | 116 | 10.4 |
| 6 | 95 | 114 | 10.4 |
| 7 | 92 | 110 | 11.5 |
| 8 | 96 | 110 | 16.9 |
| 9 | 88 | 105 | 10.1 |
| 10 | 89 | 105 | 10.9 |
| 11 | 83 | 105 | 9.9 |
| 12 | 85 | 106 | 9.3 |
| 13 | 85 | 112 | 11.2 |
| 14 | 85 | 115 | 11.1 |
| 15 | 85 | 132 | 6.6 |
| 16 | 85 | 143 | 4.3 |
| 17 | 93 | 171 | 3.4 |
| 18 | 96 | 250 | 3.8 |

Fractions 3–16 are bulked and analyzed using GLC, NMR and IR analyses confirming that the resulting material is 2-butenyl-2-ethyl-5-methyl-hex-4-enal having the structure:

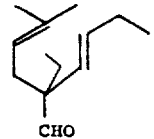

This material has a green, sweet, tomato aroma with a citrus character and a floral, rosey note becoming more rosey on dry out.

EXAMPLE V

Preparation of 2-benzyl-2-ethyl-hex-3-enal

Into a 1 liter reaction flask equipped with condenser, stirrer, thermometer, addition funnel, heating mantle and Thermo-watch is placed a solution of 85 grams sodium hydroxide in 100 grams of water. 100 Grams of toluene and 5 grams of tricapryl methyl ammonium chloride is then added and the reaction mass is heated to 70° C with stirring. While maintaining the reaction mass at 70° C, over a 5 hour period a mixture of 252 grams 2-ethyl hexenal and 235 grams benzyl chloride is added to the reaction mass. After addition is complete the reaction mass is maintained with stirring at 70° C for a period of 4 hours. At the end of this period of time the reaction mass is cooled down to 25° C and 300 ml of water is added. The organic layer is separated, and washed neutral.

After adding 15.7 grams of Primol and 2 grams of Ionox, to the residual oil, toluene is stripped off and the resulting product is then rushed over at 2.5 mm Hg to yield the following fractions:

| Fraction No. | Vapor Temperature (°C) | Liquid Temperature (°C) | Weight (g) |
|---|---|---|---|
| 1 | 47–48 | 110–80 | 106.9–30.6 |
| 2 | 113 | 117 | 31.5 |
| 3 | 120 | 127 | 55.7 |
| 4 | 121 | 123 | 49.4 |
| 5 | 122 | 123 | 49.2 |
| 6 | 122 | 123 | 39.0 |
| 7 | 125 | 125 | 33.9 |
| 8 | 126 | 133 | 50.8 |
| 9 | 138 | 164 | 25.3 |
| 10 | 225 | 205 | 15.8 |

Fractions 2–9 are bulked and after adding thereto 9.6 grams Primol and 0.8 grams Ionox, the resulting material is redistilled at a vacuum of 2.5 mm Hg at 9:1 reflux ratio on a 12 plate Vigreaux column yielding the following fractions:

| Fraction No. | Vapor Temperature (°C) | Liquid Temperature (°C) | Weight (g) |
|---|---|---|---|
| 1 | 38 | 107 | 7.2 |
| 2 | 38 | 124 | 6.5 |
| 3 | 86 | 150 | 9.2 |
| 4 | 117 | 141 | 7.1 |
| 5 | 117 | 141 | 12.8 |
| 6 | 117 | 141 | 13.8 |
| 7 | 117 | 141 | 13.5 |
| 8 | 117 | 142 | 13.6 |
| 9 | 117 | 142 | 14.9 |
| 10 | 117 | 142 | 11.2 |
| 11 | 117 | 138 | 13.0 |
| 12 | 118 | 139 | 12.9 |
| 13 | 118 | 146 | 13.5 |
| 14 | 118 | 148 | 14.1 |
| 15 | 120 | 150 | 15.8 |
| 16 | 121 | 151 | 14.8 |
| 17 | 121 | 154 | 14.7 |
| 18 | 121 | 154 | 14.2 |
| 19 | 121 | 154 | 14.8 |
| 20 | 121 | 154 | 15.3 |
| 21 | 121 | 154 | 13.9 |
| 22 | 123 | 163 | 6.6 |
| 23 | 125 | 175 | 11.4 |
| 24 | 118 | 188 | 7.0 |
| 25 | 132 | 250 | 7.7 |

Fractions 7–19 are bulked and analyzed using GLC, IR and Mass Spectral analyses which confirm that the resulting product is 2-benzyl-2-ethyl-hex-3-enal. This material has a sweet, floral, rosey note.

EXAMPLE VI

Preparation of 2-prenyl nonenal

Into a 500 ml reaction flask equipped with cooling bath, thermometer, condenser, stirrer, addition funnel and Thermowatch are placed a solution of 30.5 grams of sodium hydroxide in 30.5 grams of water. 30.5 Grams of toluene and 6 grams of tricapryl methyl ammonium chloride is then added and the mixture is cooled to 30° C. Over a 1½ hour period, a solution of 110 grams of 2-nonenal and 45 grams of prenyl chloride is added to the reaction mass. The reaction mass is then stirred for another hour at 27° C after which time 100 ml water is added. The organic layer is separated and washed neutral and the solvent stripped off.

The residual oil is then distilled through a 12 inch Vigreaux column, after adding thereto 3.5 grams of Primol and 1 gram of Ionox. The distillation data is as follows:

| Fraction No. | Vapor Temperature (°C) | Liquid Temperature (°C) | Vac. mm Hg | Weight (g) |
|---|---|---|---|---|
| 1 | 139 | 163 | 0.8 | 8.6 |
| 2 | 151 | 180 | 0.8 | 10.3 |
| 3 | 175 | 193 | 0.8 | 8.0 |
| 4 | 192 | 210 | 0.7 | 10.4 |
| 5 | 200 | 225 | 1.9 | 12.1 |

NMR, IR and Mass Spectral analyses confirm that this material is 2-prenyl nonenal having the structure:

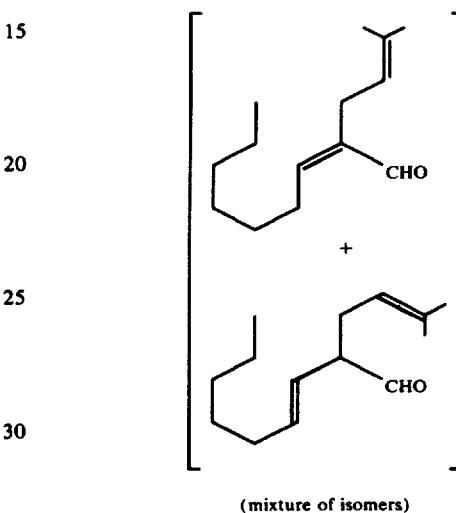

(mixture of isomers)

EXAMPLE VII

Orange terpeneless perfume formulation

The following mixture is prepared:

| Ingredient | Parts by Weight |
|---|---|
| Alcohol C₉ (n-nonanal) | 2 |
| Alcohol C₁₀ (n-decanal) | 1 |
| Alcohol C₁₂ (n-dodecanal) | 4 |
| Aldehyde C₉ (n-nonanal) | 2 |
| Aldehyde C₁₀ (n-decanal) | 3 |
| Aldehyde C₁₂ (n-dodecanal) | 1 |
| Citral | 2 |
| Methyl Anthranilate | 1 |
| Neryl Acetate | 3 |
| Geranyl Acetate | 4 |
| Terpenyl Acetate | 5 |
| Nerol | 10 |
| Terpineol | 5 |
| Geraniol | 20 |
| Linalool | 40 |
| Linalyl Acetate | 15 |
| In the alternative one of | |
| (i) 2,5-dimethyl-2-propenyl hex-4-enal; | |
| (ii) 2-methyl-2-benzyl-pent-3-enal; | |
| (iii) 2-prenyl citral; | 10 |
| (iv) 2-butenyl-2-ethyl-5-methyl hex-4-enal; | |
| (v) 2-benzyl-2-ethyl-hex-3-enal; or | |
| (vi) 2-prenyl nonenal | |

2,5-Dimethyl-2-propenyl hex-4-enal; 2-methyl-2-benzyl-pent-3-enal; 2-prenyl citral; 2-butenyl-2-ethyl-5-methyl hex-4-enal; 2-benzyl-2-ethyl-hex-3-enal; and 2-prenyl non-2-enal imparts a decided green, citrus, fruity, floral note, enhancing the orange note of this orange terpeneless perfume formulation.

EXAMPLE VIII

Preparation of 2,4,7-trimethyl-2,6-octadienal

Reaction:

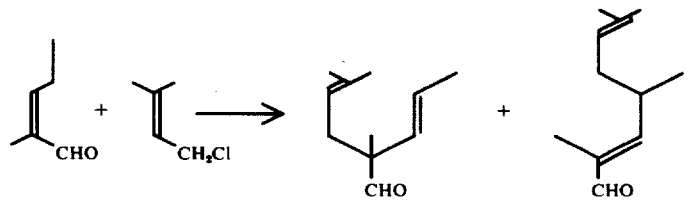

Into a 12 liter reaction flask equipped with stirrer, thermometer, reflux condenser and addition funnel is placed a solution of 720 grams of sodium hydroxide and 720 grams of water. 800 Grams of cyclohexane and 50 grams of tricapryl methyl ammonium chloride are then added to the mixture. The mixture is heated to a temperature in the range of 75°–80° C with stirring; over a period of 6 hours, a solution of 2000 grams of 2-methyl-pent-2-enal and 2100 grams of prenyl chloride is added to the reaction mass. At the end of the 6 hour period, the reaction mass is stirred at 75°–80° C for another 4 hours. At the end of the 4 hour period, the organic layer is separated, washed neutral and the solvent stripped off. The residual oil is then distilled on a rushover column after adding 82.0 grams of Primol and 6 grams of Ionox. The fractions taken off the column are as follows:

| Fraction No. | Vapor Temperature (° C) | Liquid Temperature (° C) | Vacuum mm Hg | Weight (g) |
|---|---|---|---|---|
| 1 | 42–65 | 100–100 | 120–95 | 24.7 |
| 2 | 75 | 100 | 87 | 34.8 |
| 3 | 80 | 102 | 87 | 41.7 |
| 4 | 87 | 102 | 75 | 82.7 |
| 5 | 90 | 102 | 64 | 94.9 |
| 6 | 88 | 105 | 59 | 121.1 |
| 7 | 94 | 114 | 58 | 133.8 |
| 8 | 108 | 125 | 58 | 179.4 |
| 9 | 120 | 130 | 56 | 165.2 |
| 10 | 122 | 132 | 57 | 161.5 |
| 11 | 124 | 134 | 57 | 199.5 |
| 12 | 125 | 136 | 57 | 197.4 |
| 13 | 127 | 139 | 57 | 182.3 |
| 14 | 129 | 145 | 57 | 198.5 |
| 15 | 133 | 157 | 57 | 173.1 |
| 16 | 144 | 185 | 57 | 165.8 |
| 17 | 172 | 212 | 57 | 99.0 |
| 18 | 179 | 215 | 55 | 35.1 |

Fractions 4–17 of the rushed over material are then bulked and re-distilled on an 18″ Goodloe column after adding thereto 5 grams of Ionox and 63 grams of Primol. The distillation is carried out using a reflux ratio of 9:1. The fractions distilled are as follows:

| Fraction No. | Vapor Temperature (° C) | Liquid Temperature (° C) | Vacuum mm Hg | Weight (g) |
|---|---|---|---|---|
| 1 | 49–55 | 96–97 | 50 | 14.2 |
| 2 | 59 | 100 | 50 | 27.9 |
| 3 | 60 | 104 | 50 | 40.6 |
| 4 | 60 | 109 | 50 | 45.5 |
| 5 | 66 | 120 | 50 | 85.6 |
| 6 | 100 | 124 | 50 | 56.5 |
| 7 | 113 | 125 | 50 | 27.0 |
| 8 | 118 | 125 | 50 | 27.5 |
| 9 | 118 | 125 | 50 | 89.4 |
| 10 | 95–100 | 110–110 | 25–27 | 22.0 |
| 11 | 108 | 113 | 30 | 51.8 |
| 12 | 100 | 109 | 26 | 74.9 |
| 13 | 99 | 109 | 26 | 79.0 |
| 14 | 99 | 109 | 26 | 73.0 |
| 15 | 104 | 110 | 26 | 63.1 |
| 16 | 108 | 113 | 26 | 83.8 |
| 17 | 106 | 113 | 26 | 73.4 |
| 18 | 105 | 111 | 26 | 82.3 |
| 19 | 105 | 112 | 25 | 82.4 |
| 20 | 105 | 112 | 25 | 83.5 |
| 21 | 105 | 112 | 25 | 89.7 |
| 22 | 105 | 116 | 25 | 98.4 |
| 23 | 105 | 119 | 25 | 92.0 |
| 24 | 107 | 124 | 25 | 91.1 |
| 25 | 112 | 131 | 25 | 92.8 |
| 26 | 114 | 145 | 25 | 91.5 |
| 27 | 116 | 170 | 20 | 48.6 |
| 28 | 124 | 192 | 20 | 36.5 |
| 29 | 140 | 216 | 15 | 31.8 |
| 30 | 147 | 250 | 15 | 22.7 |

Fractions 24–27 are then bulked and combined with 10 grams of Primol and 0.3 grams of Ionox. The resulting material is distilled on a 12 inch Vigreaux column equipped with heating mantle and fraction cutter. The fractionation data is as follows:

| Fraction No. | Vapor Temperature (° C) | Liquid Temperature (° C) | Vacuum mm Hg | Weight (g) | Reflux Ratio |
|---|---|---|---|---|---|
| 1 | 83–85 | 98–98 | 15–14 | 2.0 | 14:1 |
| 2 | 86 | 99 | 14 | 9.0 | 14:1 |
| 3 | 86 | 99 | 12 | 10.5 | 14:1 |
| 4 | 86 | 99 | 12 | 8.1 | 14:1 |
| 5 | 86 | 99 | 12 | 8.5 | 14:1 |
| 6 | 88 | 99 | 12 | 14.4 | 14:1 |
| 7 | 85 | 99 | 12 | 7.3 | 14:1 |
| 8 | 85 | 99 | 12 | 6.2 | 14:1 |
| 9 | 85 | 99 | 12 | 11.3 | 14:1 |
| 10 | 85 | 99 | 12 | 11.3 | 14:1 |
| 11 | 85 | 99 | 12 | 14.1 | 14:1 |
| 12 | 85 | 99 | 12 | 15.4 | 14:1 |
| 13 | 85 | 102 | 12 | 14.5 | 14:1 |
| 14 | 83–85 | 99–101 | 10–10 | 4.8 | 12:1 |
| 15 | 90 | 104 | 12 | 8.3 | 12:1 |

-continued

| Fraction No. | Vapor Temperature (° C) | Liquid Temperature (° C) | Vacuum mm Hg | Weight (g) | Reflux Ratio |
|---|---|---|---|---|---|
| 16 | 89 | 104 | 13 | 9.9 | 12:1 |
| 17 | 82 | 104 | 12 | 7.0 | 12:1 |
| 18 | 87 | 105 | 12 | 12.8 | 12:1 |
| 19 | 90 | 105 | 11 | 11.2 | 12:1 |
| 20 | 92 | 105 | 11 | 9.6 | 12:1 |
| 21 | 94 | 105 | 11 | 8.6 | 12:1 |
| 22 | 94 | 105 | 11 | 11.9 | 12:1 |
| 23 | 94 | 105 | 11 | 15.8 | 12:1 |
| 24 | 94 | 105 | 11 | 16.9 | 12:1 |
| 25 | 94 | 105 | 11 | 14.6 | 12:1 |
| 26 | 94 | 105 | 11 | 15.8 | 12:1 |
| 27 | 94 | 105 | 11 | 14.4 | 12:1 |
| 28 | 94 | 119 | 11 | 8.4 | 12:1 |
| 29 | 100 | 140 | 11 | 5.7 | 12:1 |
| 30 | 108 | 220 | 11 | 5.7 | 12:1 |

Fraction 26 of the resulting distillate is then chromatographed on a GLC column (conditions: ¼ inch × 10 feet; 5% Carbowax 20M [adsorbed on Chromasorb G] column programmed at 10°C/minute from 80°–220° C) indicating a major component of 90% purity. NMR, Mass Spectral and IR analyses yield the information that this major component is 2,4,7-trimethyl-2,6-octadienal.

Figure 2:
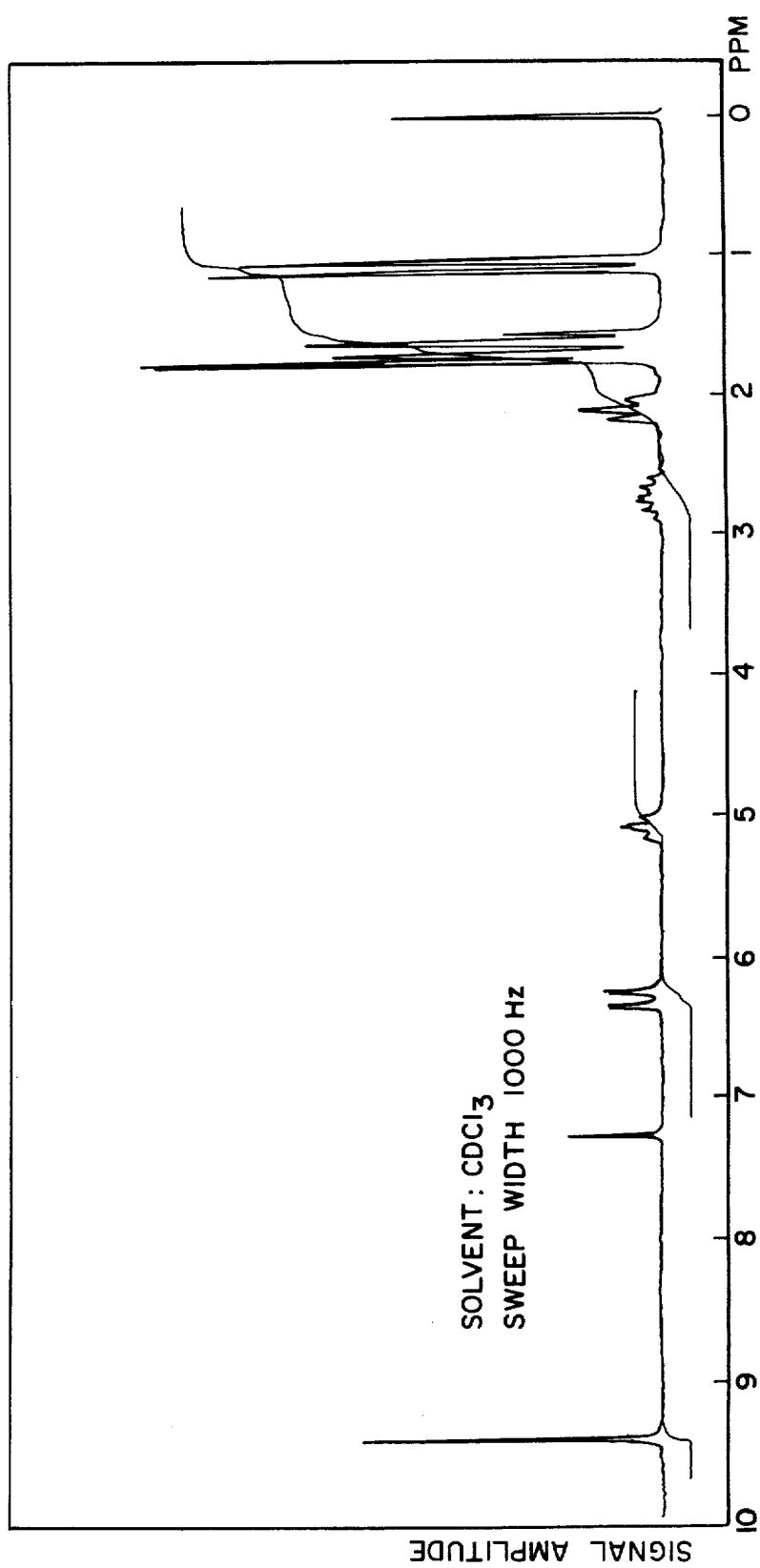
Figure 3:
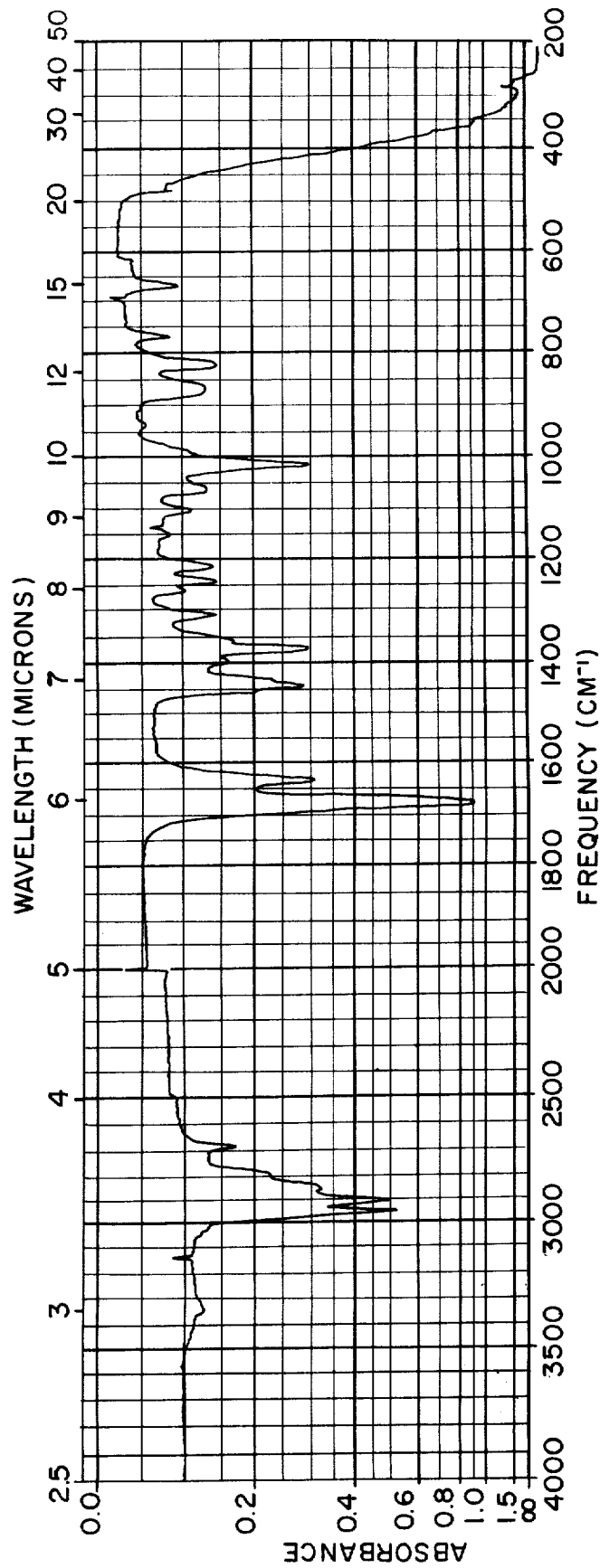

The NMR spectrum for fraction 26, major peak, is set forth in FIG. 2. The IR spectrum for fraction 26, major peak, is set forth in FIG. 3.

EXAMPLE IX

Mandarin orange flavor formulation

An orange flavor formulation is prepared by admixing:

| Ingredients | Parts |
|---|---|
| Natural orange oil | 13.00 |
| Acetaldehyde | 1.50 |
| Ethyl acetate | 0.10 |
| Ethyl butyrate | 0.50 |
| Propanal | 0.10 |
| Trans-2-hexenal | 0.10 |
| Ethyl alcohol (95%) | 60.00 |
| Fusel oil | 0.05 |
| Propylene glycol | 24.65 |

This is denominated Flavor A. A second formulation, Flavor B is prepared by adding 2,4,7-trimethyl-2,6-octadienal produced according to Example VIII (one percent in ethanol) to a portion of Flavor A.

Each of Flavors A and B is added in the amount of 2 ounces per gallon of 32° Baume sugar syrup to produce a syrup for combination with water to form a drink. The beverage prepared using Flavor A is a passable orange beverage of good character, flavor and intensity.

The beverage prepared using flavor B has a much improved mandarin orange flavor with new mandarin orange and lemony nuances.

What is claimed is:

1. A process for preparing at least one aldehyde represented by the structure:

$$R_2-\underset{\underset{\gamma}{H}}{\overset{R_4}{\underset{|}{C}}}-\underset{\beta}{\overset{R_3}{\underset{|}{C}}}-\underset{\alpha}{\overset{|}{\underset{R_1}{C}}}-C\overset{\displaystyle O}{\underset{\displaystyle H}{\diagdown\!\!\!\!/}}$$

comprising the step of intimately admixing a halide having the structure $R_1X$ wherein X is chloro with an unsaturated aldehyde having the structure:

$$R_2-\overset{H}{\underset{H}{\overset{|}{C}}}-\overset{R_4}{\underset{}{\overset{|}{C}}}=\overset{R_3}{\underset{}{\overset{|}{C}}}-C\overset{\displaystyle O}{\underset{\displaystyle H}{\diagdown\!\!\!\!/}}$$

in the presence of an alkali metal hydroxide, an inert solvent and a "phase transfer agent", wherein one of the dashed lines is a double bond and the other of the dashed lines is a single bond; wherein $R_1$ is prenyl or benzyl, $R_2$ is methyl, n-propyl, 4-methyl-3-pentenyl or n-hexyl, and $R_3$ and $R_4$ are each the same or different and are hydrogen, methyl or ethyl with the proviso that when $R_3$ is methyl or ethyl the dashed line between the beta carbon atom and the gamma carbon atom represents a double bond and when $R_3$ is hydrogen, either of the dashed lines is a double bond; said phase transfer agent having the structure:

$$\left[\begin{array}{c}R'_1\\R'_4-\underset{|}{\overset{|}{N}}-R'_2\\R'_3\end{array}\right]^+ Z^-$$

wherein at least one of the groups $R'_1$, $R'_2$, $R'_3$ and $R'_4$ is $C_6$–$C_{14}$ alkaryl or $C_6$–$C_{20}$ alkenyl, and the other of $R'_1$, $R'_2$, $R'_3$ and $R'_4$ is $C_1$–$C_8$ alkyl, and Z represents halogen, the temperature of the reaction being in the range of from about 10° up to about 150° C, the mole ratio of unsaturated aldehyde:halide being from 0.5:1.5 up to about 1.5:0.5, the mole ratio of alkali metal hydroxide:halide being from about 0.75:1 up to about 1.5:1 and the concentration of "phase transfer agent" in grams per mole of unsaturated aldehyde being from 0.5 up to 25.

2. The process of claim 1 wherein $R_1$ is prenyl, $R_2$ is methyl, $R_3$ is methyl and $R_4$ is hydrogen.

3. The process of claim 1 wherein $R_1$ is benzyl, $R_2$ is methyl, $R_3$ is methyl and $R_4$ is hydrogen.

4. The process of claim 1, wherein $R_1$ is prenyl, $R_2$ is n-propyl, $R_3$ is ethyl and $R_4$ is hydrogen.

5. The process of claim 1 wherein $R_1$ is benzyl, $R_2$ is n-propyl, $R_3$ is ethyl and $R_4$ is hydrogen.

6. The process of claim 1 wherein $R_1$ is prenyl, $R_2$ is 4-methyl-3-pentenyl, $R_3$ is hydrogen and $R_4$ is methyl.

7. The process of claim 1 wherein $R_1$ is prenyl, $R_2$ is n-hexyl, $R_3$ is hydrogen and $R_4$ is hydrogen.

* * * * *